United States Patent
Durand et al.

(10) Patent No.: US 11,484,269 B2
(45) Date of Patent: Nov. 1, 2022

(54) SYSTEMS AND METHODS FOR CHRONIC NEURAL RECORDING

(71) Applicant: Case Western Reserve University, Cleveland, OH (US)

(72) Inventors: Dominique M. Durand, Solon, OH (US); Grant McCallum, South Euclid, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 882 days.

(21) Appl. No.: 16/335,331

(22) PCT Filed: Dec. 6, 2016

(86) PCT No.: PCT/US2016/065111
§ 371 (c)(1),
(2) Date: Mar. 21, 2019

(87) PCT Pub. No.: WO2018/057047
PCT Pub. Date: Mar. 29, 2018

(65) Prior Publication Data
US 2020/0015754 A1     Jan. 16, 2020

Related U.S. Application Data

(60) Provisional application No. 62/399,714, filed on Sep. 26, 2016.

(51) Int. Cl.
*H01B 11/06*     (2006.01)
*A61B 5/00*     (2006.01)
(Continued)

(52) U.S. Cl.
CPC .............. *A61B 5/7207* (2013.01); *A61B 5/24* (2021.01); *A61B 5/273* (2021.01); *A61B 5/313* (2021.01);
(Continued)

(58) Field of Classification Search
CPC ... H01B 7/02; H01B 7/04; H01B 7/18; H01B 11/02; H01B 11/06; H01R 11/01;
(Continued)

(56) References Cited

U.S. PATENT DOCUMENTS 3,654,933 A     4/1972   Hagfors
3,738,368 A     6/1973   Avery et al.
(Continued)

FOREIGN PATENT DOCUMENTS

EP          0199216 A     3/1989
WO     2003/058646 A1     7/2003

OTHER PUBLICATIONS

Andersen, Mads P., et al. "Chronic cuff electrode recordings from walking Gottingen mini-pigs." 2011 Annual International Conference of the IEEE Engineering in Medicine and Biology Society. IEEE, 2011.
(Continued)

*Primary Examiner* — William H. Mayo, III
(74) *Attorney, Agent, or Firm* — Tarolli, Sundheim, Covell & Tummino LLP

(57) ABSTRACT

A system for reducing and/or eliminating noise in chronic neural recording of low amplitude neural signals from conscious, freely-moving subjects. Triboelectric noise effects are reduced or eliminated using in implant lead with insulating materials with charge affinities separated by 10 nC/J or less. The recording device can include a preamplifier device that uses capacitors with a low-distortion dielectric material.

19 Claims, 2 Drawing Sheets

(51) Int. Cl.
  *A61B 5/24* (2021.01)
  *H01B 7/00* (2006.01)
  *H01B 1/00* (2006.01)
  *A61B 5/313* (2021.01)
  *A61B 5/273* (2021.01)

(52) U.S. Cl.
  CPC .............. *A61B 5/686* (2013.01); *H01B 1/00* (2013.01); *H01B 7/00* (2013.01); *H01B 11/06* (2013.01); *A61B 2562/0209* (2013.01); *A61B 2562/222* (2013.01)

(58) Field of Classification Search
  CPC ......... H01R 43/28; A61B 3/1455; A61B 5/24; A61B 5/273; A61B 5/7207; A61B 5/686
  USPC .......... 174/102 R, 104, 105 R, 110 R, 113 R
  See application file for complete search history.

(56) References Cited

U.S. PATENT DOCUMENTS

| | | | |
|---|---|---|---|
| 3,774,618 A | 11/1973 | Avery | |
| 6,870,109 B1* | 3/2005 | Villarreal | A61B 5/24 174/102 R |
| 2008/0057779 A1* | 3/2008 | Mastrototaro | H01R 11/01 439/502 |
| 2008/0255435 A1* | 10/2008 | Al-Ali | A61B 5/14551 600/323 |
| 2011/0220389 A1* | 9/2011 | Huang | H01B 11/203 174/113 R |
| 2011/0315426 A1* | 12/2011 | Wandler | H01B 11/1066 174/113 R |

OTHER PUBLICATIONS

Andreasen, Lotte NS, and Johannes J. Struijk. "Artefact reduction with alternative cuff configurations." IEEE transactions on biomedical engineering 50.10 (2003): 1160-1166.
Foretius, Tim, et al. "A transverse intrafascicular multichannel electrode (TIME) to interface with the peripheral nerve." Biosensors and Bioelectronics 26.1 (2010): 62-69.
Branner, Almut, et al. "Long-term stimulation and recording with a penetrating microelectrode array in cat sciatic nerve." IEEE transactions on biomedical engineering 51.1 (2004): 146-157.
Chomiak, Taylor, and Bin Hu. "What is the optimal value of the g-ratio for myelinated fibers in the rat CNS? A theoretical approach." PloS one 4.11 (2009): e7754.
Craggs, Michael D. The cortical control of limb protheses. Diss. King's College London (University of London), 1974.
De Campos, Deivis, et al. "Degree of myelination (g-ratio) of the human recurrent laryngeal nerve." European Archives of Oto-Rhino-Laryngology 271.5 (2014): 1277-1281.
Dhillon, Gurpreet S., et al. "Residual function in peripheral nerve stumps of amputees: implications for neural control of artificial limbs." The Journal of hand surgery 29.4 (2004): 605-615.
Ducker, Thomas B., George J. Hayes, and Brigadier General. "Experimental improvements in the use of Silastic cuff for peripheral nerve repair." Journal of neurosurgery 28.6 (1968): 582-587.
Dweiri, Yazan M., et al. "Ultra-low noise miniaturized neural amplifier with hardware averaging." Journal of neural engineering 12.4 (2015): 046024.
Dweiri, Yazan M., et al. "Fabrication of high contact-density, flat-interface nerve electrodes for recording and stimulation applications." JoVE (Journal of Visualized Experiments) 116 (2016): e54388.
Edell, David J. "A peripheral nerve information transducer for amputees: long-term multichannel recordings from rabbit peripheral nerves." IEEE Transactions on Biomedical Engineering 2 (1986): 203-214.
Grill, Warren M., and J. Thomas Mortimer. "Neural and connective tissue response to long-term implantation of multiple contact nerve cuff electrodes." Journal of Biomedical Materials Research: An Official Journal of The Society for Biomaterials, The Japanese Society for Biomaterials, and The Australian Society for Biomaterials and the Korean Society for Biomaterials 50.2 (2000): 215-226.
Gustafson, Kenneth J., et al. "Fascicular anatomy of human femoral nerve: implications for neural prostheses using nerve cuff electrodes." Journal of rehabilitation research and development 46.7 (2009): 973.
Harreby, Kristian R., et al. "Subchronic stimulation performance of transverse intrafascicular multichannel electrodes in the median nerve of the Göttingen minipig." Artificial organs 39.2 (2015): E36-E48.
Haughland, Morten. "A flexible method for fabrication of nerve cuff electrodes." Proceedings of 18th Annual International Conference of the IEEE Engineering in Medicine and Biology Society. vol. 1. IEEE, 1996.
Haughland, Morten K., and Thomas Sinkjaer. "Cutaneous whole nerve recordings used for correction of footdrop in hemiplegic man." IEEE Transactions on rehabilitation Engineering 3.4 (1995): 307-317.
Hoffer, J. A., G. E. Loeb, and C. A. Pratt. "Single unit conduction velocities from averaged nerve cuff electrode records in freely moving cats." Journal of neuroscience methods 4.3 (1981): 211-225.
Julien, C., and S. Rossignol. "Electroneurographic recordings with polymer cuff electrodes in paralyzed cats." Journal of neuroscience methods 5.3 (1982): 267-272.
Kato, Naoki, et al. "Critical role of p38 MAPK for regeneration of the sciatic nerve following crush injury in vivo." Journal of neuroinflammation 10.1 (2013): 757.
Kozai, Takashi D. Yoshida, et al. "Ultrasmall implantable composite microelectrodes with bioactive surfaces for chronic neural interfaces." Nature materials 11.12 (2012): 1065.
Kundu, Aritra, et al. "Stimulation selectivity of the "thin-film longitudinal intrafascicular electrode"(tfLIFE) and the "transverse intrafascicular multi-channel electrode"(TIME) in the large nerve animal model." IEEE transactions on neural systems and rehabilitation engineering 22.2 (2013): 400-410.
Loeb, G. E., and R. A. Peck. "Cuff electrodes for chronic stimulation and recording of peripheral nerve activity." Journal of neuroscience methods 64.1 (1996): 95-103.
Micera, Silvestro, et al. "Decoding information from neural signals recorded using intraneural electrodes: toward the development of a neurocontrolled hand prosthesis." Proceedings of the IEEE 98.3 (2010): 407-417.
Micera, Silvestro, et al. "On the use of longitudinal intrafascicular peripheral interfaces for the control of cybernetic hand prostheses in amputees." IEEE Transactions on Neural Systems and Rehabilitation Engineering 16.5 (2008): 453-472.
Milner, Theodore E., et al. "Cutaneous afferent activity in the median nerve during grasping in the primate." Brain research 548.1-2 (1991): 228-241.
Musick, Katherine M., et al. "Chronic multichannel neural recordings from soft regenerative microchannel electrodes during gait." Scientific reports 5 (2015): 14363.
Naples, Gregory G., et al. "A spiral nerve cuff electrode for peripheral nerve stimulation." IEEE transactions on biomedical engineering 35.11 (1988): 905-916.
Navarro, Xavier, et al. "A critical review of interfaces with the peripheral nervous system for the control of neuroprostheses and hybrid bionic systems." Journal of the Peripheral Nervous System 10.3 (2005): 229-258.
Nikolic, Zoran M., et al. "Instrumentation for ENG and EMG recordings in FES systems." IEEE transactions on biomedical engineering 41.7 (1994): 703-706.
Ochoa, J., T. J. Fowler, and Roger W. Gilliatt. "Anatomical changes in peripheral nerves compressed by a pneumatic tourniquet." Journal of Anatomy 113.Pt 3 (1972): 433.
Ogata, Kosuke, and Masatoshi Naito. "Blood flow of peripheral nerve effects of dissection stretching and compression." The Journal of Hand Surgery: British & European vol. 11.1 (1986): 10-14.

(56) References Cited

OTHER PUBLICATIONS

PCT International Search Report and Written Opinion for corresponding International Application Serial No. PCT/US2016/065111, dated May 29, 2017, pp. 1-8.
Pudenz, R. H., L. A. Bullara, and A. Talalla. "Electrical stimulation of the brain. I. Electrodes and electrode arrays." Surgical neurology 4.1 (1975): 37-42.
Rahal, Mohamad, et al. "An improved configuration for the reduction of EMG in electrode cuff recordings: a theoretical approach." IEEE transactions on biomedical engineering 47.9 (2000): 1281-1284.
Raspopovic, Stanisa, et al. "Restoring natural sensory feedback in real-time bidirectional hand prostheses." Science translational medicine 6.222 (2014): 222ra19-222ra19.
Rieger, Robert, et al. "Design of a low-noise preamplifier for nerve cuff electrode recording." IEEE Journal of Solid-State Circuits 38.8 (2003): 1373-1379.
Riso, Ronald R., et al. "Nerve cuff recordings of muscle afferent activity from tibial and peroneal nerves in rabbit during passive ankle motion." IEEE Transactions on Rehabilitation Engineering 8.2 (2000): 244-258.
Rozman, Janez, Bojan Zorko, and Matjazunc Bunc. "Selective recording of electroneurograms from the sciatic nerve of a dog with multi-electrode spiral cuffs." The Japanese journal of physiology 50.5 (2000): 509-514.
Rydevik, B., G. Lundborg, and U. Bagge. "Effects of graded compression on intraneural blood flow: An in vivo study on rabbit tibial nerve." The Journal of hand surgery 6.1 (1981): 3-12.
Sadeghlo, Bita, and Paul B. Yoo. "Enhanced electrode design for peripheral nerve recording." 2013 6th International IEEE/EMBS Conference on Neural Engineering (NER). IEEE, 2013.
Sahin, Mesut, Dominique M. Durand, and Musa A. Haxhiu. "Chronic recordings of hypoglossal nerve activity in a dog model of upper airway obstruction." Journal of Applied Physiology 87.6 (1999): 2197-2206.
Schiefer, Matthew A., et al. "Selective stimulation of the human femoral nerve with a flat interface nerve electrode." Journal of neural engineering 7.2 (2010): 026006.
Schuettler, M., et al. "Fabrication of implantable microelectrode arrays by laser cutting of silicone rubber and platinum foil." Journal of neural engineering 2.1 (2005): S121.
Sharma, Asha, et al. "Long term in vitro functional stability and recording longevity of fully integrated wireless neural interfaces based on the Utah Slant Electrode Array." Journal of neural engineering 8.4 (2011): 045004.
Sinha, Gunjan. "Charged by GSK investment, battery of electroceuticals advance." (2013): 654.
Stein, Richard B., et al. "Stable long-term recordings from cat peripheral nerves." Brain research 128.1 (1977): 21-38.
Stieglitz, Thomas, Martin Schuettler, and J-Uwe Meyer. "Micromachined, polyimide-based devices for flexible neural interfaces." Biomedical microdevices 2.4 (2000): 283-294.
Struijk, Johanna Jan, and Morten Thomsen. "Tripolar nerve cuff recording: stimulus artifact, EMG and the recorded nerve signal." Proceedings of 17th International Conference of the Engineering in Medicine and Biology Society. vol. 2. IEEE, 1995.
Tan, Daniel W., et al. "A neural interface provides long-term stable natural touch perception." Science translational medicine 6.257 (2014): 257ra138-257ra138.
Tang, Yuang, B. Wodlinger, and D. M. Durand. "Bayesian spatial filters for source signal extraction: A study in the peripheral nerve." IEEE Transactions on Neural Systems and Rehabilitation Engineering 22.2 (2014): 302-311.
Tyler, Dustin J., and Dominique M. Durand. "Functionally selective peripheral nerve stimulation with a flat interface nerve electrode." IEEE Transactions on Neural Systems and Rehabilitation Engineering 10.4 (2002): 294-303.
Tyler, Dustin J., and Dominique M. Durand. "Chronic response of the rat sciatic nerve to the flat interface nerve electrode." Annals of biomedical engineering 31.6 (2003): 633-642.
Van Der Puije, P. D., R. Shelley, and G. E. Loeb. "A self-spiraling thin-film nerve cuff electrode." Proc. 19th Canadian Medical and Biological Engineering Conference. 1993.
Wodlinger, Brian. Extracting Command Signals from Peripheral Nerve Recordings. Diss. Case Western Reserve University, 2010.
Wodlinger, Brian, and Dominique M. Durand. "Localization and recovery of peripheral neural sources with beamforming algorithms." IEEE Transactions on Neural Systems and Rehabilitation Engineering 17.5 (2009): 461-468.
Yoo, Paul B., Mesut Sahin, and Dominique M. Durand. "Selective stimulation of the canine hypoglossal nerve using a multi-contact cuff electrode." Annals of biomedical engineering 32.4 (2004): 511-519.

\* cited by examiner

SYSTEMS AND METHODS FOR CHRONIC NEURAL RECORDING

RELATED APPLICATIONS

This application claims the benefit of U.S. Provisional Application No. 62/399,714, entitled "ELECTRODE ASSEMBLY," filed Sep. 26, 2016. The entirety of this provisional application is hereby incorporated by reference for all purposes.

TECHNICAL FIELD

The present disclosure relates generally to chronic neural recording of conscious, freely-moving subjects and, more specifically, to systems and methods for reducing or eliminating noise effects during the chronic recording of low amplitude neural signals.

BACKGROUND

Neural signals are typically characterized by a low voltage amplitude signal, often on the order of microvolts or lower. Accordingly, to record these neural signals, a recording assembly system that minimizes and/or eliminates all ambient noise sources, which can be perceived as false positive signals of interest, is required. However, for chronic neural recordings suffer from a motion artifact that is not minimized and eliminated due to the recording assembly system. Noise due to this motion artifact can be on the order of microvolts, often obscuring the recorded neural signal.

SUMMARY

The present disclosure relates generally to chronic neural recording of conscious, freely-moving subjects. Such chronic neural recordings can be obstructed by different motion artifacts. Two major sources of these motion artifacts include triboelectric noise caused by the implant lead and audiophonic noise caused by the recording device. More specifically, the present disclosure relates to systems and methods for reducing or eliminating these noise effects during the chronic recording of low amplitude neural signals.

In one aspect, the present disclosure can include an implant lead for transmitting a low amplitude neural signal. The implant lead can include a tube having a lumen and a plurality of insulated wires disposed in the lumen to transmit the neural recording signal. Each of the insulated wires can include a conductive wire and an insulating layer encircling the conductive wire to insulate the conductive wire. Each of the insulating layers and the tube comprise materials with charge affinities separated by 10 nC/J or less to reduce triboelectric noise in the neural recording signals.

In another aspect, the present disclosure can include a system that can be used for chronic neural recording. The system can include a plurality of sensors to detect low amplitude signals, each of the sensors to record a low amplitude signal, a recording device to receive the plurality of low amplitude signals recorded by the plurality of sensors, and an implant lead to transmit the plurality of low amplitude signals from the plurality of sensors to the recording device. The implant lead including: a tube having a lumen; and a plurality of insulated wires disposed in the lumen. Each of the insulated wires made of a conductive wire; and an insulating layer encircling the conductive wire to insulate the conductive wire. Each of the insulating layers and the tube comprise materials with charge affinities that are separated by 10 nC/J or less to reduce triboelectric noise. In some instances, audiophonic noise can be reduced in the recording device by using a pre-amplifier device that uses special low distortion capacitors (e.g., with a low distortion dielectric material).

In a further aspect, the present disclosure can include a method for chronic neural recording. The method can include recording, by a plurality of implanted sensors, a plurality of low amplitude signals. The plurality of low amplitude signals can be transmitted by a plurality of insulated wires within an implant lead to a receiver device. The implant lead can include the plurality of insulated wires bundled within a tube. The insulated wires each comprising a conductive wire and an insulating layer encircling the conductive wire to insulate the conductive wire. Each of the insulating layers and the tube including materials with charge affinities separated by 10 nC/J or less to reduce triboelectric noise. In some instances, audiophonic noise can be reduced in the recording device by using a pre-amplifier device that uses special low distortion capacitors (e.g., with a low distortion dielectric material).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
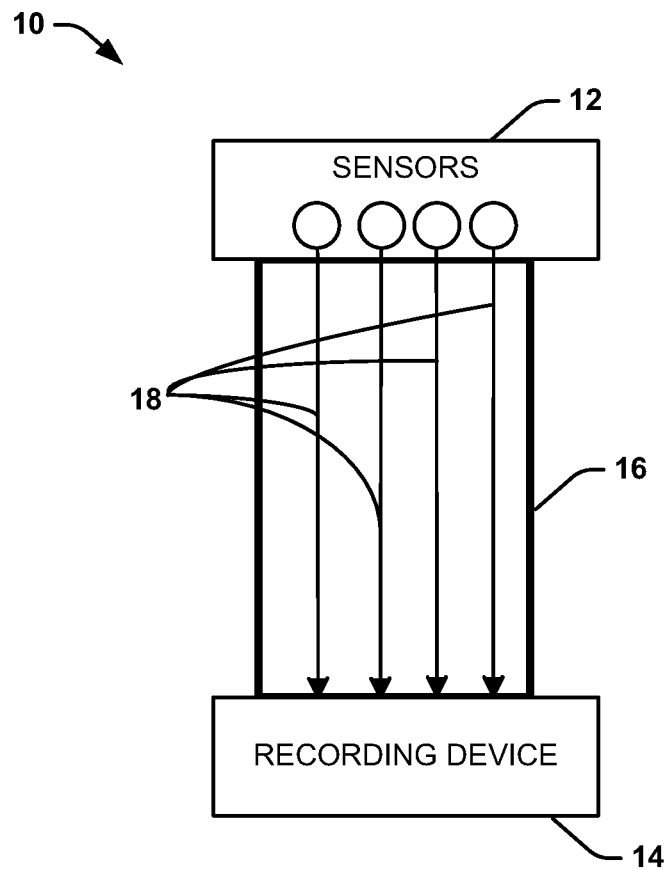
FIG. 1 is a schematic diagram showing a system that can be used for chronic neural recording in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "chronic" neural recording can refer to a recording from a subject's neural tissue taken over an extended time period. During a chronic neural recording, the subject can be conscious and freely-moving.

As used herein, the term "neural tissue" can refer tissue that is specialized for the conduction of electrical impulses that convey information or instructions from one region of the body to another via one or more nerves. As examples, the neural tissue can include nerves of the peripheral nervous system, nerves of the central nervous system, or any muscle innervated by a nerve.

As used herein, the term "nerve" can refer to one or more fibers that employ electrical and chemical signals to transmit motor, sensory, and/or autonomic information from one body part to another. A nerve can refer to either a component of the central nervous system or the peripheral nervous system.

As used herein, the term "noise effects" can refer to can refer to any type of artifact or other irregular fluctuation that accompanies a transmitted electrical signal, but is not part of the electrical signal and tends to obscure the electrical signal. A type of noise effect dealt with herein can be referred to as a motion artifact. Examples of different noise effects that can be attributed to a motion artifact during chronic neural recording can include triboelectric noise, audiophonic noise, noise from a high impedance ground path, electromagnetic noise, or the like.

As used herein, the term "triboelectric effect" can refer to a type of contact electrification due to electron transfer as a result of two materials coming into contact (e.g., frictional contact) with one another and then separating.

As used herein, the term "triboelectric noise" can refer to a type of noise (e.g., a motion artifact) due to the triboelectric effect.

As used herein, the term "charge affinity" (also referred to as "electron affinity") can refer to the amount of energy released or spent to add an electron to a neural atom. Charge affinity can be expressed in a unit of nC/J.

As used herein, the unit "nC/J" can refer to nano-coulombs (or nano-ampere-second) of transferred charge per Joule (watts-second or Newton-meter) of friction energy applied between surfaces.

As used herein, the term "insulating material" can refer to any material that does not readily conduct electricity.

As used herein, the term "conductive material" can refer to any material that conducts electricity.

As used herein, the term "audiophonic noise" can refer to artifacts cased by the piezo-electric effect of capacitors (especially the AC-coupling capacitors) in response to vibration of an acquisition circuit of a recording device during movement of the subject.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to chronic neural recording of conscious, freely-moving subjects. Chronic neural recording can involve transmission of low amplitude neural signals via an implant lead that connects a one or more sensors (e.g., recording electrodes) at a distal end to acquisition electronics of a receiving device at the proximal end. More specifically, the present disclosure relates to systems and methods for reducing or eliminating noise effects during the chronic recording of low amplitude neural signals. These noise effects can arise at least from the implant lead, the acquisition electronics of the recording device, the ground path from the acquisition electronics of the recording device to the subject, and/or an apparatus used by the freely-moving subject. The most significant noise effects can be triboelectric noise within the implant lead and audiophonic noise due to the acquisition electronics of the recording device.

Triboelectric noise can arise in the implant lead when dissimilar insulating materials having charge affinities that are greatly different are used on the individual wires and/or a tube encasing the wires. One example configuration of a traditional implant lead can include a plurality of conductive stainless-steel wires that are individually insulated with a Teflon coating, bundled, and then placed in a silicone tube. However, these dissimilar insulating materials rub against each other, charge transfer can occur between the insulating materials and into the lead's conductive core, resulting in voltage spikes. This charge transfer is due to the large difference in charge affinity between silicone (+6 nC/J) and Teflon (−190 nC/J). Charge affinity arises from the fact that some materials like to give away electrons (+ charge affinity), while others will freely accept electrons (− charge affinity). The larger the charge affinity difference two adjacent materials have the greater amount of charge exchanged upon momentary contact. This triboelectric noise can be reduced or eliminated if the implant lead were made of insulating materials that with similar or equivalent charge affinities. In another example, the triboelectric noise can be reduced or eliminated by adding a polymer (e.g., a conductive polymer) to the implant lead to limit the relative movement of the dissimilar insulating materials and, thereby, limit the triboelectric noise.

The large voltage spikes (e.g., up to 100 μV) of audiophonic noise can arise in the acquisition electronics recording device due to the piezo-electric effect of capacitors in response to acquisition circuit vibration during movement. The audiophonic noise can be reduced or eliminated by using a special capacitor with a low distortion dielectric material. Less significant noise effects can include the ground path from the acquisition electronics of the recording device to the subject, and/or an apparatus used by the freely-moving subject. The noise effects can be reduced or eliminated by decreasing the impedance of the ground path and/or eliminating the electromagnetic noise source.

III. Systems

One aspect of the present disclosure can include a system 10 (FIG. 1) that can be used for chronic neural recording. The system can include an implant lead to transmit neural signals recorded by sensors 12 to a recording device 14. Advantageously, the implant lead can transmit the neural signals with reduced or eliminated triboelectric noise compared to traditional leads with Teflon-encased wires bundled in a silicone tube. An additional advantage of the system 10 is that the recording device 14 can reduce or eliminate audiophonic noise due to the piezo-electric effect of capacitors (especially the AC-coupling capacitors) in response to vibration of the acquisition circuit of the recording device 14 during movement of the subject.

The sensors 12 can include a plurality of sensor elements that can each record a neural signal. The sensor elements can each be electrical sensors (e.g., electrodes), chemical sensors, resistive sensors, pressure sensors, or the like. As an example, the sensor elements can be a plurality of electrodes for neural recording, such as electrode contacts of a nerve cuff electrode. However, the sensor elements can be implanted sensors, body surface sensors, or a combination or implanted and body surface sensors. Although four sensor elements are shown in FIG. 1, it will be understood that any number of sensor elements greater than 1 can be employed by the sensors 12.

The recording device 14 can receive the neural signals from the sensors 12. For example, the recording device 14 can process and/or display the neural signals. In some instances, the recording device 14 can include additional circuitry or software to facilitate the processing and/or display of the neural signals. To this end, the recording device 14 can include a non-transitory memory storing software instructions and a processor to execute the software instructions to facilitate the processing and/or display of the neural signals. Additionally, the recording device 14 can include one or more amplifiers and/or other circuitry that can process the neural signals for analysis.

As an example, the recording device 14 can include a preamplifier device that serves as the acquisition circuit to receive the recorded signal and an amplifier that can amplify the received signal. In chronic neural recordings, the preamplifier can experience audiophonic noise due to the piezo-electric effect of solder joints from capacitors in the signal path that inject charge during movement resulting in spike artifacts (that can be as high as 100 µV), which can be further amplified by the amplifier circuit. Eliminating this noise source can be critical in chronic neural recordings where the subject has the ability to freely move. Accordingly, recording device 14 employs a preamplifier with capacitors using a low-distortion dielectric material. One example of such a capacitor that uses a low-distortion dielectric material is a low-distortion ceramic capacitor that is available from Taiyo Yuden Co. Ltd.

The system 10 can include an implant lead that can transmit the neural signals from the sensors 12 to the recording device 14. The neural signals transmitted by the implant lead can be on the order of microvolts. During chronic recordings, the neural signals transmitted through the implant lead can be subject to a motion artifact due to triboelectric noise (due to two insulating materials rubbing together during motion). The triboelectric noise can obscure the recorded neural signal. For example, the triboelectric noise can be on the order of microvolts or greater. To reduce or eliminate triboelectric noise due to the motion artifact, each of the two insulating materials can be made of materials with similar charge affinities.

The implant lead can be any lead connecting the sensors 12 to the recording device 14. The implant lead, in some instances, can include a plurality of insulated wires 18 spanning between each sensor 12 and the recording device 14. Although four wire/sensor pairs are shown, there could be any number of insulated wires spanning between each sensor 12 and the recording device 14.

Particularly, the implant lead can be subject to continuous or nearly continuous motion for periods of time. Additionally, the implant lead can carry low level (e.g., low amplitude) signals, such as neural recordings. As an example, the implant lead can be used to transmit neural signals from implanted sensors to an external recording device. Using the implant lead described herein, very low amplitude signals recorded by sensors 12 can be transmitted faithfully to a recording device 14.

Figure 2:
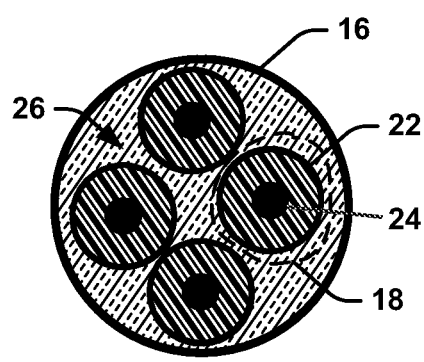
FIG. 2 illustrates an example cut out of an implant lead that can be used in connection with the system in FIG. 1.

An example cut out of the implant lead is shown in FIG. 2. The implant lead can include a tube 16 having a lumen and a plurality of insulated wires 18 disposed in the lumen to transmit the neural recording signals. However, the tube 16 with the lumen is not strictly necessary for the plurality of insulated wires 18. Although four insulated wires 18 are shown in FIGS. 1 and 2, it will be understood that the implant lead can include any number of insulated wires greater than 1 and equal to the number of sensor elements employed by the sensors 12. For example, each of the plurality of insulated wires 18 can be configured to carry a neural signal from one of the sensor elements to the recording device 14.

The tube 16 can be made of an insulating material and used for structural purposes. The insulated wires 18 can be bundled together and disposed within the lumen of the tube 16. For example, the tube 16 can be used to ensure that the insulated wires 18 stay together and do not separate between the sensors 12 on the subject and the recording device 14. Each of the insulated wires 18 can include a wire 24 of a conductive material encircled by an insulating layer 22 of an insulating material encircling the wire 24. The insulating layer 22 can provide insulation to the wire 24. The insulating layer 22 need not be made of the same material for every wire 24, but the materials used for insulation should have a similar (e.g., 10 nC/J or less difference) or equivalent charge affinity (shown in Table 1 below) to reduce or eliminate triboelectric noise due to a motion artifact.

Additionally, when the tube 16 is used, to reduce or eliminate triboelectric noise due to a motion artifact, the insulating layers 22 and the tube 16 can have a similar charge affinity (shown in Table 1 below).

TABLE 1

Triboelectric Table showing charge affinity values for different materials.

| Material | Affinity (nC/J) |
| --- | --- |
| Polyurethane foam | +60 |
| Sorbothane | +55 |
| Box sealing tape (BOPP) | +55 |
| Hair, oily skin | +45 |
| Solid Polyurethane, filled | +40 |
| Magnesium fluoride (MgF$_2$) | +35 |
| Nylon, dry skin | +30 |
| Machine oil | +29 |
| Nylatron | +28 |
| Glass (soda) | +25 |
| Paper (uncoated copy) | +10 |
| Wood (pine) | +7 |
| GE brand Silicone II | +6 |
| Cotton | +5 |
| Nitrile rubber | +3 |
| Wool | 0 |
| Polycarbonate | −5 |
| ABS | −5 |
| Acrylic (PMMA), adhesive side of clear and office tape | −10 |
| Epoxy | −32 |
| Styrene-butadiene rubber | −35 |
| Solvent-based spray paint | −38 |
| PET (mylar) cloth and solid | −40 |
| EVA rubber, filled | −55 |
| Gum rubber | −60 |
| Hot melt glue | −62 |
| Polystyrene | −70 |
| Polyimide | −70 |
| Silicones (not GE) | −72 |
| Vinyl | −75 |
| Carton-sealing tape (BOPP), sanded | −85 |
| Olefins | −90 |
| Cellulose nitrate | −93 |
| Office tape backing | −95 |

TABLE 1-continued

Triboelectric Table showing charge affinity values for different materials.

| Material | Affinity (nC/J) |
| --- | --- |
| UHMWPE | −95 |
| Neoprene | −98 |
| PVC | −100 |
| Latex rubber | −105 |
| Viton, filled | −117 |
| Epichlorohydrin rubber, filled | −118 |
| Santoprene rubber | −120 |
| Hypalon rubber, filled | −130 |
| Butyl rubber, filled | −135 |
| EDPM rubber, filled | −140 |
| Teflon | −190 |

When two different materials are placed side by side and pressed or rubbed together, electrons can move from one surface of one material to another depending on their relative charge affinity. Using insulating layers 22 and/or the tube 16 with similar charge affinities can reduce the likelihood of developing a triboelectric charge, and according triboelectric noise, due to a motion artifact. To reduce or eliminate triboelectric noise, the insulating materials should have charge affinities as close as possible.

For example, each of the insulating layers 22 and/or the tube 16 can be made of materials with charge affinities separated by 10 nC/J or less. In some instances, each of the insulating layers 22 and/or the tube 16 can be made of materials with charge affinities separated by 5 nC/J or less. In other instances, each of the insulating layers 22 and/or the tube 16 can be made of materials with charge affinities separated by 2 nC/J or less. In still other instances, each of the insulating layers 22 and/or the tube 16 can be made of materials with equal (or identical) charge affinities. An example implant lead that would be acceptable can be an implant lead where the tube 16 is a Teflon tube and the insulating layers 22 are Teflon.

Alternatively, if the insulating layers 22 and/or the tube 16 cannot be made of materials with similar charge affinity (e.g., if different wires with different insulators are used), relative motion therebetween can be eliminated. This relative motion can be eliminated by filling segments 26 with a polymer material to limit the relative movement of these dissimilar materials. In another alternate example, the tube 16 can be eliminated. As a further alternate example, the segments 26 can be filled with a conductive polymer material (or other conductive medium) between to direct charge away from the conductive lead wire. In an additional example, the tube 16 can be made with a material with a − charge affinity, while the insulating layers 22 can be made with a material with a + charge affinity.

IV. Methods

Figure 3:
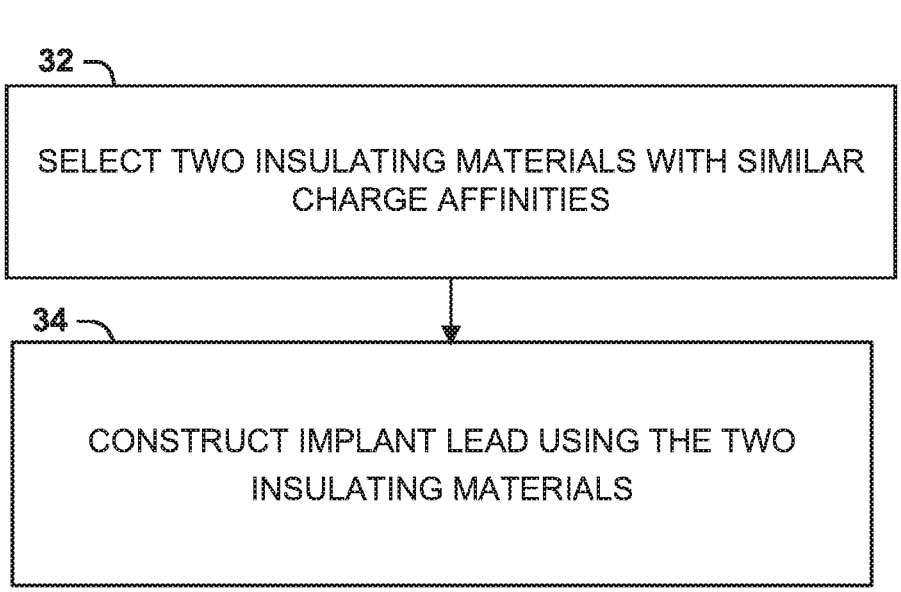
FIG. 3 is a process flow diagram illustrating a method for constructing an implant lead according to another aspect of the present disclosure.
Figure 4:
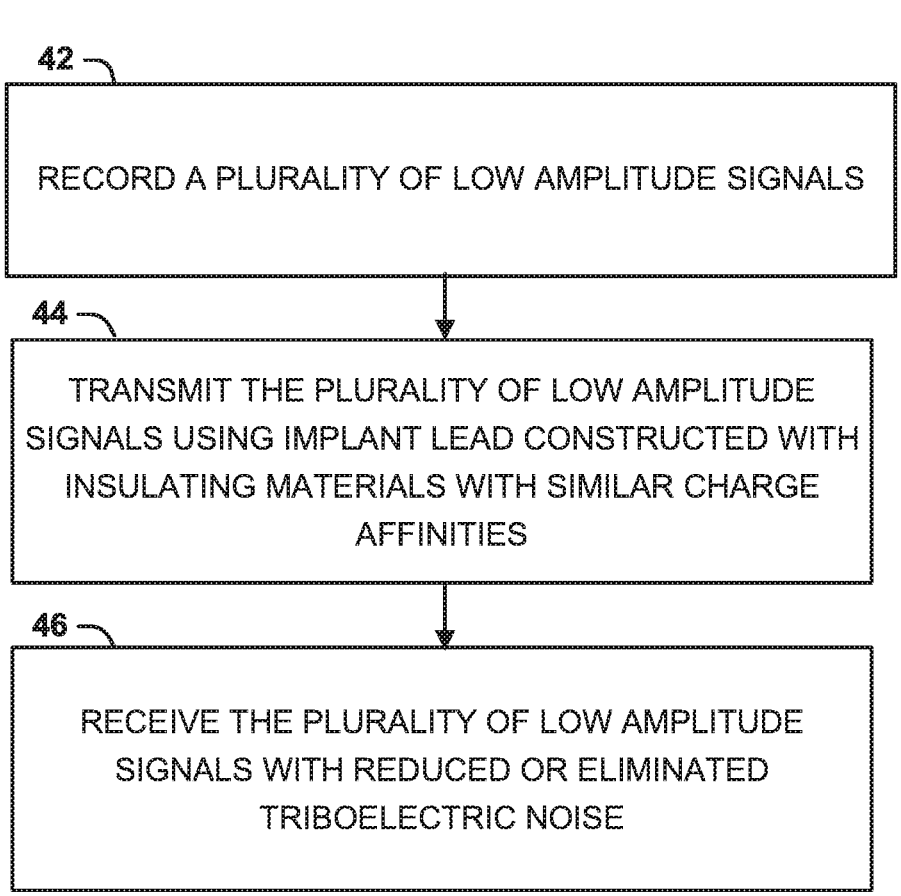
FIG. 4 is a process flow diagram illustrating a method for chronic neural recording using the implant lead constructed according to the method of FIG. 3.

Another aspect of the present disclosure can include methods that can be used to facilitate chronic neural recording. FIG. 3 illustrates a method 30 for constructing an implant lead that can be used during chronic neural recording to reduce triboelectric noise. For example, the implant lead constructed according to method 30 can be the implant lead shown in FIGS. 1 and 2. FIG. 4 illustrates a method 40 for chronic neural recording using the implant lead constructed according to the method 30 of FIG. 3. For example, the method 40 of FIG. 4 can be conducted by the system 10 shown in FIG. 1. Additionally, the method 40 of FIG. 4 can further eliminate audiophonic noise by using special low-distortion capacitors in the preamplifier device to reduce the effects of motion of the subject.

The methods 30 and 40 are illustrated as process flow diagrams with flowchart illustrations. For purposes of simplicity, the methods 30 and 40 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30 and 40.

Referring now to FIG. 3, illustrated is a method 30 for constructing an implant lead. At step 32, two (or more) insulating materials with similar charge affinities can be selected. In fact, to reduce or eliminate contamination with triboelectric noise (a motion artifact) during signal transmission through the implant lead, the insulating materials should have charge affinities as close as possible. For example, each of the two materials can have charge affinities separated by 10 nC/J or less. In some instances, each of the two materials can have charge affinities separated by 5 nC/J or less. In other instances, each of the two materials can have charge affinities separated by 2 nC/J or less. In still other instances, each of the two materials can have equal (or identical) charge affinities.

At step 34, the implant lead can be constructed using the two (or more) insulating materials. For example, the implant lead can be constructed with conductive wires insulated by one of the two insulating materials. The insulated conductive wires can be grouped together into a tube of the other insulating material. As another example, the wires can be insulated by each of the two insulating materials without the tube. With the two insulating materials having charge affinities that are very close together, the triboelectric noise due to friction or other motion-induced artifacts can be reduced or eliminated.

Referring now to FIG. 4, illustrated is a method 40 for chronic neural recording using the implant lead constructed according to the method 30. At step 42, a plurality of low amplitude signals can be recorded. For example, the low amplitude signals can be electromyogram (EMG) signals or other neural signals. At step 44, the plurality of low amplitude signals can be transmitted using the implant lead constructed with the two insulating materials with similar charge affinities (e.g., chosen with the method 30 of FIG. 3). At step 46, the plurality of low amplitude signals can be received with reduced or eliminated triboelectric noise. In some instances, the receiver can further eliminate audiophonic noise by using special low-distortion capacitors in a preamplifier device to reduce the effects of motion of the subject.

From the above description, those skilled in the art will perceive improvements, changes and modifications. Such improvements, changes and modifications are within the skill of one in the art and are intended to be covered by the appended claims.

The following is claimed:

1. An implant lead comprising:
   a tube made of an insulating material and having a lumen; and
   a plurality of insulated wires disposed in the lumen, each of the plurality of insulated wires is configured to transmit low amplitude neural recording signals, each of the insulated wires comprising:
   a conductive wire; and
   an insulating layer encircling the conductive wire to insulate the conductive wire;

wherein each of the insulating layers and the tube comprise materials with charge affinities separated by 10 nC/J or less to reduce an amount of triboelectric noise in the neural recording signals by reducing an amount of triboelectric charge created when the insulating layers and the tube rub against each other.

2. The implant lead of claim 1, wherein each of the insulating layers and the tube comprise materials with identical charge affinities.

3. The implant lead of claim 2, wherein the materials with identical charge affinities eliminate the triboelectric noise from the neural recording signals.

4. The implant lead of claim 1, wherein the neural recording signals comprise an amplitude on the order of the triboelectric noise or less.

5. A system comprising:
an implant lead comprising:
a tube made of an insulating material and having a lumen; and
a plurality of insulated wires disposed in the lumen, each of the plurality of insulated wires configured to transmit low amplitude neural recording signals and comprising:
a conductive wire; and
an insulating layer encircling the conductive wire to insulate the conductive wire;
a plurality of sensors to detect the low amplitude neural recording signals, each of the plurality of sensors being electrically connected to one of the plurality of insulated wires; and
a recording device connected to each of the plurality of insulated wires to receive the low amplitude neural recording signals,
wherein each of the insulating layers and the tube comprise materials with charge affinities separated by 10 nC/J or less to reduce an amount of triboelectric noise in the low amplitude signals by reducing an amount of triboelectric charge created when the insulating layers and the tube rub against each other.

6. The system of claim 5, wherein the recording device is configured to reduce audiophonic noise.

7. The system of claim 6, wherein the recording device comprises a preamplifier device with capacitors comprising a low-distortion dielectric material.

8. The system of claim 5, wherein each of the insulating layers and the tube comprise materials with charge affinities separated by 5 nC/J or less.

9. The system of claim 5, wherein each of the insulating layers and the tube comprise materials with identical charge affinities.

10. The system of claim 9, wherein the materials with identical charge affinities eliminate the triboelectric noise from the plurality of low amplitude neural recording signals.

11. The system of claim 5, wherein each of the insulating layers comprises Teflon and the tube is a Teflon tube.

12. The system of claim 5, wherein the recording device comprises an amplifier to amplify the plurality of low amplitude neural recording signals.

13. A method comprising:
recording, by a plurality of implanted sensors, a plurality of low amplitude neural recording signals;
transmitting, by a plurality of insulated wires within an implant lead, the plurality of low amplitude neural recording signals recorded by the plurality of implanted sensors,
wherein the implant lead comprises the plurality of insulated wires bundled within a lumen of a tube made of an insulated material, the insulated wires each comprising a conductive wire and an insulating layer encircling the conductive wire to insulate the conductive wire, each of the insulating layers and the tube comprising materials with charge affinities separated by 10 nC/J or less to reduce an amount of triboelectric noise in the neural recording signals by reducing an amount of triboelectric charge created when the insulating layers and the tube rub against each other; and
receiving, at a receiver device, the plurality of low amplitude neural recording signals.

14. The method of claim 13, wherein each of the insulated wires and the tube comprise materials with charge affinities separated by 10 nC/J or less.

15. The method of claim 13, wherein each of the insulated wires and the tube comprise materials with charge affinities separated by 5 nC/J or less.

16. The method of claim 13, wherein each of the insulated wires and the tube comprise materials with identical charge affinities.

17. The method of claim 16, wherein the materials with identical charge affinities eliminate the triboelectric noise in the plurality of low amplitude neural recording signals.

18. The method of claim 13, wherein the receiver device comprises an amplifier to amplify the low amplitude signals.

19. The method of claim 13, wherein the receiver device comprises a preamplifier device with capacitors comprising a low-distortion dielectric material.

* * * * *